United States Patent
Mori

(10) Patent No.: US 7,199,089 B2
(45) Date of Patent: Apr. 3, 2007

(54) LIQUID PREPARATION FOR CONTACT LENS COMPRISING A DISINFECTANT AND BUFFER MIXTURE

(75) Inventor: Osamu Mori, Kasugai (JP)

(73) Assignee: Menicon Co., Ltd., Nagoya (JP)

( * ) Notice: Subject to any disclaimer, the term of this patent is extended or adjusted under 35 U.S.C. 154(b) by 0 days.

(21) Appl. No.: 11/334,080

(22) Filed: Jan. 18, 2006

(65) Prior Publication Data

US 2006/0122080 A1    Jun. 8, 2006

Related U.S. Application Data

(63) Continuation of application No. PCT/JP04/07923, filed on Jun. 7, 2004.

(30) Foreign Application Priority Data

Aug. 20, 2003  (JP) .............................. 2003-295863

(51) Int. Cl.
*C11D 1/62* (2006.01)
*C11D 3/20* (2006.01)

(52) U.S. Cl. ...................... 510/112; 510/253; 510/131; 510/382; 510/384; 510/391; 510/499; 510/504; 134/901

(58) Field of Classification Search ................ 510/112, 510/253, 131, 382, 384, 391, 499, 504
See application file for complete search history.

(56) References Cited

U.S. PATENT DOCUMENTS

| | | | |
|---|---|---|---|
| 6,319,464 B1 * | 11/2001 | Asgharian | 422/28 |
| 6,419,962 B1 * | 7/2002 | Yokoyama et al. | 424/725 |
| 6,528,048 B1 * | 3/2003 | Koike et al. | 424/78.17 |
| 6,806,243 B2 * | 10/2004 | Hozumi et al. | 510/112 |
| 2003/0153622 A1 | 8/2003 | Hozuumi et al. | |
| 2004/0185028 A1 * | 9/2004 | Hu et al. | 424/78.27 |
| 2005/0042198 A1 * | 2/2005 | Smith et al. | 424/78.38 |

FOREIGN PATENT DOCUMENTS

| | | |
|---|---|---|
| EP | 0 888 780 A1 | 1/1999 |
| EP | 1 050 304 | 11/2000 |
| GB | 2 090 013 A1 | 6/1982 |
| JP | 57-132115 A1 | 8/1982 |
| JP | 10-108899 A1 | 4/1998 |
| JP | 10-137327 A1 | 5/1998 |
| JP | 11-052308 A1 | 2/1999 |
| JP | 11-249087 A1 | 9/1999 |
| JP | 2000-513001 A1 | 10/2000 |
| JP | 2001-242428 A1 | 9/2001 |
| JP | 2002-136578 A1 | 5/2002 |
| JP | 2003-116972 A1 | 4/2003 |
| JP | 2003-160482 A1 | 6/2003 |
| WO | WO 98/25649 A1 | 6/1998 |
| WO | 98/50084 | 11/1998 |

\* cited by examiner

*Primary Examiner*—Charles Boyer
(74) *Attorney, Agent, or Firm*—Burr & Brown

(57) ABSTRACT

A liquid preparation for a contact lens is provided, including at least one disinfectant selected from the group consisting of germicidal biguanides and germicidal quaternary ammonium salts (Component A), glycolic acid and/or asparatic acid (Component B), and 2-amino-2-methyl-1,3-propanediol or a salt thereof (Component C). Component B and Component C are provided in a sufficient amount to fulfill a predetermined molar ratio.

11 Claims, No Drawings

LIQUID PREPARATION FOR CONTACT LENS COMPRISING A DISINFECTANT AND BUFFER MIXTURE

This application is a continuation of the International Application No. PCT/JP2004/007923, filed Jun. 7, 2004, which claims the benefit under 35 U.S.C. §119(a)–(d) of Japanese Application 2003-295863, filed Aug. 20, 2003, the entireties of which are incorporated herein by reference.

TECHNICAL FIELD

The present invention relates in general to a liquid preparation for a contact lens, and more particularly, to a liquid preparation which is advantageously used as a contact lens solution for sterilizing, disinfecting, cleaning, and storing the contact lens.

BACKGROUND ART

Generally, contact lenses are classified into non-water-based contact lenses and water-based contact lenses, hard contact lenses and soft contact lenses, or nonionic contact lenses and ionic contact lenses. During a long period of use of the contact lenses, microorganisms such as bacteria and fungi tend to adhere to and proliferate on the surfaces of the contact lenses while the contact lenses are stored after they have been removed from the eyes. In view of the above, contact lenses generally need to be sterilized before they are worn on the eyes. In particular, it is especially important to sterilize soft contact lenses since microorganisms are more likely to proliferate on the surfaces of soft contact lenses than on hard contact lenses, increasing the risk of causing infectious diseases.

For this reason, conventionally used liquid preparations for contact lens, in which predetermined disinfectants (preservatives) are included, for thereby executing the sterilizing treatments have been used. As the disinfectants to be added to the liquid preparations for contact lens, biguanide compounds whose typical example is polyhexamethylene biguanide (PHMB) and quaternary ammonium compounds whose typical examples are benzalkonium chloride and polyquaternium, are widely used, for instance, because these disinfectants have especially effective disinfecting properties compared to those of other disinfectants.

However, for assuring practical requirements in view of disinfection (preservation), it is necessary to increase the amount of the disinfectants to be included in the liquid preparation, even if the above-mentioned effective disinfectants are used. If the disinfectant is used in a high concentration, however, it is toxic to the eyes, and the disinfectant is easily adsorbed on the contact lens, which causes eye troubles such as eye irritation, and gives rise to a problem of insufficient safety. In view of this, various studies have been made to provide a liquid preparation for a contact lens that is capable of exhibiting a higher disinfecting effect while reducing the amount of the disinfectant that is required.

For example, JP-A-10-108899 proposed a liquid preparation for a contact lens which includes, in addition to 0.1 ppm to 10 ppm of polyhexamethylene biguanide, a nonionic isotonic agent within a sufficient ratio to provide a certain extent of an osmotic pressure, which extent is similar to that of a predetermined concentration of sodium chloride. In JP-A-11-249087, a liquid preparation for a contact lens is proposed, which includes a nonionic isotonic agent and/or an amino acid, in addition to a predetermined polyquaternium. It is true that the disinfecting effect of the liquid preparation for contact lens can be improved by adopting this constitution of the liquid preparation. However, there is an inherent problem in that, depending on the kind of nonionic isotonic agent and/or the amino acid to be used, the contact lens, especially a soft contact lens, swells or shrinks, so that the size of the contact lens is changed, whereby the specification of the contact lens is changed.

For this reason, in order to restrict changes in the size of the contact lens to be within an extent that does not substantially obstruct the wearing of the contact lens, JP-A-2001-242428 and JP-A-2002-136578 explain that it is useful to further add an amino-acid salt, in particular a sodium salt of an amino acid, to the liquid preparation for the contact lens, in addition to the above-mentioned components.

The inventors of the present invention, together with other inventors, previously proposed in JP-A-2003-160482, a liquid preparation for contact lens, which includes: a germicidal biguanide or a germicidal quaternary ammonium salt; a predetermined amino acid (salt); and a predetermined acidic compound having a carboxyl group or a phosphoric acid group, wherein the concentration of sodium chloride is 0 to 0.2% by weight. It is disclosed that, by using the liquid preparation for contact lens, the adsorption of the disinfectant on the contact lens is restricted. Due to this, safety to the eyes is assured, and swelling and shrinkage of the contact lens is prevented, whereby the problem of changes in the size of the contact lens can be advantageously solved.

However, further studies regarding the liquid preparation for a contact lens by the inventors of the present invention have newly revealed that a problem of precipitation or deposition of crystals and powdery substances on the contact lens may be caused, depending on the combination of components used. In detail, if the contact lens, especially a soft contact lens, is immersed in a liquid preparation which is obtained by combining PHMB, arginine, and glycolic acid or asparatic acid for a long period of time, or if the contact lens is repeatedly immersed in the liquid preparation, white crystals or white powdery substances, which are assumed to be derived from components of the liquid preparation, may be deposited on the surfaces of the contact lens in a dot-like form. If the components of the liquid preparation are deposited on the contact lens as described above, the field of view of the contact lens is deteriorated, which adversely affects the optical characteristics of the lens. In addition, deposits such as crystals and powdery substances cause irritation to the eyes, easily adhering the deposits to the lens, and so on. Therefore, further improvements to the liquid preparation for a contact lens are required from the point of view of preventing the deposition of components of the liquid preparation.

There can be listed the followings, as the prior art documents related to the present invention.

Patent document 1: JP-A-10-108899
Patent document 2: JP-A-11-249087
Patent document 3: JP-A-2000-242428
Patent document 4: JP-A-2002-136578
Patent document 5: JP-A-2003-160482
Patent document 6: JP-A-10-137327
Patent document 7: JP-A-11-52308
Patent document 8: JP-A-2000-513001
Patent document 9: JP-A-57-132115

SUMMARY OF THE INVENTION

The present invention was developed in the light of the situations described above. One object of the present invention is to provide a liquid preparation for a contact lens, wherein the liquid preparation for the contact lens assures an excellent disinfecting effect and provides a sufficiently high degree of safety to the eyes of the lens wearer so that the liquid preparation for the contact lens does not adversely affect the contact lens, such as by changing the size of the contact lens, and so that the liquid preparation for the contact lens advantageously restrains the generation of deposits on the lens.

The inventors of the present invention have made extensive research in an effort to solve the above-indicated problem, and found that by adding glycolic acid and/or asparatic acid, which are/is acidic compound(s), and 2-amino-2-methyl-1,3-propanediol (salt) to a liquid preparation for contact lens including a germicidal biguanide and/or a germicidal quaternary ammonium salt, so as to fulfill a predetermined ratio of these components, an excellent disinfecting effect and safety are assured, changes of the lens size are advantageously restricted, and the generation of deposits on the lens can be effectively prevented.

According to a first aspect of the present invention, a liquid preparation for a contact lens is provided, comprising a component (A) which is at least one disinfectant selected from the group consisting of germicidal biguanides and germicidal quaternary ammonium salts, a component (B) which is glycolic acid and/or asparatic acid, and a component (C) which is 2-amino-2-methyl-1,3-propanediol or a salt thereof. The molar ratio of components B and C is in a range of 1:20 to 1.3:1.

According to a second aspect of the present invention, the concentration of sodium chloride in the liquid preparation is adjusted to be in a range of 0 to 0.2 w/w %.

According to a third aspect of the present invention, the component A is included in the liquid preparation in a concentration of 0.1 to 500 ppm.

According to a fourth aspect of the present invention, the component B is included in the liquid preparation in a concentration of 0.01 to 5 w/w %.

According to a fifth aspect of the present invention, a neutral amino acid is further included.

According to a sixth aspect of the present invention, the neutral amino acid is preferably included in the liquid preparation in a concentration of 0.1 to 4 w/w %.

According to a seventh aspect of the present invention, the neutral amino acid is glycine.

According to an eighth aspect of the present invention, propylene glycol is preferably further included in the liquid preparation.

According to a ninth aspect of the present invention, the propylene glycol is included in the liquid preparation in a concentration of 0.1 to 1 w/w %.

According to a tenth aspect of the present invention, at least one of a surfactant and a chelating agent is further included in the liquid preparation.

According to an eleventh aspect of the present invention, the contact lens to be treated with the preparation is a soft contact lens.

In the above-mentioned first aspect of the present invention, glycolic acid and/or asparatic acid (component B) are used, which generate an organic anion by ionizing in an aqueous medium, in addition to the germicidal biguanide and/or the germicidal quaternary ammonium salt (component A). Due to this, the adsorption of the disinfectant on the contact lens is advantageously restricted, and the liquid preparation offers excellent safety to the eyes.

In the first aspect, 2-amino-2-methyl-1,3-propanediol or the salt thereof (component C) is further added to the liquid preparation in addition to the above-mentioned components A and B, wherein component C is added to the liquid preparation in a sufficient amount to satisfy a predetermined molar ratio for components B and C. Due to this, an advantageous disinfecting effect is realized, and an excellent disinfecting effect can be obtained. In addition, due to the combined use of components B and C, changes in the size of the contact lens are advantageously restricted, and generation of deposits on the contact lens derived from the liquid preparation are also effectively prevented.

In detail, the above-mentioned component A exists in the aqueous medium in the form of a cation, so that component A is easily attached to or adsorbed on the contact lens, especially an ionic contact lens having a negative charge. However, as component B, which is ionized in the aqueous medium and generates an organic anion, is added to the liquid preparation, the adsorption of component A on the contact lens is restricted, whereby safety to the eyes is advantageously enhanced. However, the above-mentioned organic anion (component B) has a tendency to influence the cation (component A), so that the disinfecting effect of component A is disturbed. Meanwhile, in the present invention, component C, which is ionized in the aqueous medium and generates am organic cation, is further added to the liquid preparation, so as to satisfy the predetermined ratio of components B and C. Due to this, the obstruction to the disinfection caused by component B is advantageously reduced, whereby the disinfecting effect of component A can be effectively realized. If component B or component C is independently added to the liquid preparation, thus obtained liquid preparation has a tendency to cause shrinkage or swelling of the lens. Meanwhile, in the present invention, component B and component C are combined together and used in a predetermined molar ratio, so that changes in the size of the lens are effectively prevented, and an excellent compatibility with the lens can be realized. Moreover, even if the contact lens is immersed in the liquid preparation for the contact lens including the above-mentioned components A to C for a long period of time, or if the contact lens is repeatedly immersed in the liquid preparation, components originating from the liquid preparation are not deposited on the surfaces of the contact lens.

In the second aspect of the liquid preparation for contact lens of the present invention, an effective disinfecting effect is exhibited, so that an excellent disinfecting effect can be advantageously realized.

According to the third aspect of the present invention, the content of the disinfectant is extremely small. Even if the content of the disinfectant is kept to a small amount as described above, the intended disinfecting effect can still be advantageously realized, and provides remarkably excellent safety to the eyes.

In addition, according to the above-mentioned fourth aspect of the liquid preparation for contact lens of the present invention, component B (as the essential component) is added to the liquid preparation in a predetermined concentration, so that the above-mentioned effects of the present invention, e.g., the effect of solving problems such as the generation of the deposits, can be further advantageously realized.

Moreover, in the fifth to seventh aspects of the present invention, the above-mentioned effects attributed to the present invention can be further advantageously exhibited.

In addition, according to the eighth and ninth aspects of the present invention, the lipophilicity of the liquid preparation for the contact lens is improved, so that occurrences of eye irritation are more advantageously restricted, and enhanced comfort can be obtained. Moreover, it is also possible to lower the cost of the liquid preparation.

In addition, according to the tenth aspect of the liquid preparation for contact lens of the present invention, further effects according to the additional components are added to the liquid preparation.

Moreover, according to the eleventh aspect of the present invention, a soft contact lens is treated with the liquid preparation for a contact lens according to the present invention. As described above, in the present invention, the above-mentioned effects are advantageously exhibited to the soft contact lens, as well.

DETAILED DESCRIPTION OF THE INVENTION

The liquid preparation for a contact lens according to the present invention is constituted by a water-based aqueous medium containing a predetermined disinfectant or a preservative (component A), to which there are added: glycolic acid and/or asparatic acid (component B); and 2-amino-2-methyl-1,3-propanediol (AMPD) or a salt thereof (component C), wherein components B and C are combined with each other to fulfill a predetermined ratio of these components.

It is desirable that the above-mentioned disinfectant (component A) has an excellent disinfecting effect and conformity with the contact lens and the eyes, and it is still more desirable that the disinfectant is not likely to cause troubles such as allergies. At least one of, or any combination of conventionally known germicidal biguanides and germicidal quaternary ammonium salts can be used as the disinfectant. In particular, germicidal biguanides are especially advantageously used, because the disinfecting effect of germicidal biguanides is not likely to be obstructed by other liquid components, such as component B, so that even a small amount of germicidal biguanides can provide an excellent disinfecting effect compared with germicidal quaternary ammonium salts.

Examples of germicidal biguanides include polyhexamethylene biguanide (PHMB) and biguanide polymer, which is represented by the following formula (1).

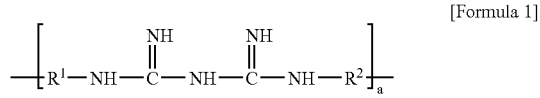

[Formula 1]

wherein "a" represents an integer not smaller than 1; and wherein $R^1$ and $R^2$ each independently represent a divalent group represented by CnHmOp, wherein n=1~24, m=2~48, and p=0~11.

Examples of germicidal quaternary ammonium salts include: tetraalkyl ammonium salts such as alkyltrimethylammonium chlorides; alkyl ammonium salt such as trialkylbenzyl ammonium salts such as octadecyldimethylbenzylammonium chloride; quaternary salts of alkylhydroxy alkylimidazoline whose typical example is hydroxyethyl alkylimidazoline chloride; alkylisoquinolinium salts whose typical example is alkylisoquinolinium bromide; alkylpyridinium salts and cationic surfactants such as amideamines. In addition to the above, polymeric quaternary ammonium compounds represented by the following formulas (2) to (4), a condensation product of diamines and a dihalogen compound, as disclosed in the Japanese Patent No. 2550036, and a polycationic compounds as disclosed in JP-A-4-231054, JP-A-8-512145, and JP-A-11-249087, cationic cellulose polymer, such as Polyquaternium-4 and Polyquaternium-10, and benzalkonium halide may also be used.

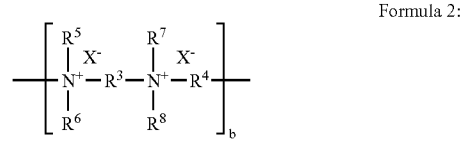

Formula 2:

wherein "b" represents an integer not smaller than 1; $X^-$ is a monovalent anion such as $Cl^-$; $R^3$ and $R^4$ each independently represent a divalent group represented by CnHmOp, wherein n=1~24, m=2~48, and p=0~11; and $R^5$, $R^6$, $R^7$ and $R^8$ each independently represent a monovalent group represented by CqHrOs, wherein q=1~4, r=2~9, and s=0~1.

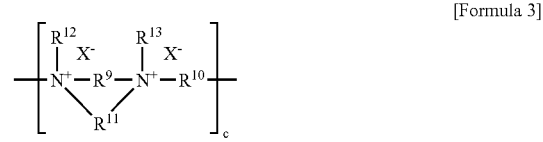

[Formula 3]

wherein "c" represents an integer not smaller than 1; $X^-$ is a monovalent anion such as $Cl^-$; $R^9$ and $R^{10}$ each independently represent a divalent group represented by CnHmOp, wherein n=1~24, m=2~48, and p=0~11; $R^{11}$ represents a monovalent group represented by CtHuOv, wherein t=1~4, u=2~9, and v=0~1; and $R^{12}$ and $R^{13}$ each independently represent a monovalent group represented by CqHrOs, wherein q=1~4, r=2~9, and s=0~1.

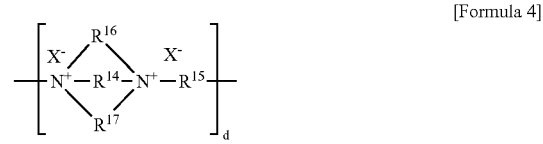

[Formula 4]

wherein "d" represents an integer not smaller than 1; $X^-$ is a monovalent anion such as $Cl^-$; $R^{14}$ and $R^{15}$ each independently represent a divalent group represented by CnHmOp, wherein n=1~24, m=2~48, and p=0~11; and each of $R^{16}$ and $R^{17}$ independently represents a divalent group represented by CtHuOv, wherein t=1~4, u=2~9, and v=0~1.

The content of the above-mentioned component A is not particularly limited. Generally, a sufficient disinfecting or preservative effect can be obtained by using component A within a range of about 0.1 to about 1000 ppm. In the present invention, within the above-mentioned concentration range, there can be advantageously adopted a low concentration, i.e., 0.1 to 500 ppm, more preferably 0.1 to 200 ppm. In the present invention, an advantageous disinfecting effect can be obtained, even if the concentration of component A is very low. If the content of component A is smaller than the above-mentioned concentration range, a sufficient disinfecting (preservative) effect cannot be obtained. On the other hand, if the content of component A exceeds the above-mentioned upper limit of the concentration range, problems with regard to safety can be caused, such as adverse effects to the eyes and the adsorption of component A on the surfaces of the contact lens can be accelerated.

Meanwhile, in the liquid preparation for contact lens according to the present invention, one or both glycolic acid and asparatic acid are included as component B. In these two acid compounds, glycolic acid is more preferably used, because glycolic acid does not lower the disinfecting effect of component A as much as asparatic acid does. A part or all of component B is ionized in the aqueous medium to generate the organic anion. Due to this, component A, which exists as a cation in the aqueous medium, is effectively restrained from adsorbing on the contact lens. Accordingly, occurrences of eye troubles, such as inflammation and full-staining of the cornea can be advantageously prevented, wherein the entire surface of the cornea is stained by fluorescein during the corneal staining test, so that safety to the eyes is highly advantageously assured.

The amount of component B to be included is suitably determined so as to advantageously restrict the adsorption of component A on the contact lens. It is generally desirable that component B is included within a range of 0.01 to 5 w/w % (percent by weight), and preferably 0.05 to 1 w/w %. This is because, if the amount of component B included in the liquid preparation is excessively small, the effect of restricting the adsorption of component A on the contact lens cannot be expected. On the other hand, if the amount of component B is excessively large, the contact lens shrinks and the size of the contact lens changes, causing problems in wearing the contact lens.

As mentioned above, by using component B, attachment of component A to the contact lens is restricted, and excellent safety to the eyes is realized. However, a mere combination of component A and component B tends to result in shrinking the contact lens and reduces the disinfecting effect by disturbing the disinfecting effect of component A, which generates the cation in the aqueous medium. For this reason, in the present invention, component C, which will be described later, is also included in the liquid preparation for a contact lens as one of the essential components.

In other words, in the liquid preparation for a contact lens in accordance with the present invention, 2-amino-2-methyl-1,3-propanediol (AMPD) or a salt thereof is included as component C. As the salt of AMPD, hydrochlorides can be used, for instance.

If component C is added to the liquid preparation, a part or all of component C is ionized in the aqueous medium and an organic cation is generated. This organic cation works on the above-mentioned organic anion of component B, whereby the deterioration of the disinfecting effect and the shrinkage of the contact lens caused by component B are advantageously restricted. Therefore, the disinfecting effect of component A can be advantageously exhibited, and changes in the size of the contact lens are effectively prevented.

The prevention of changes in the size of the contact lens is presumed to be due to the following effects. That is, the liquid preparation for a contact lens which includes component B without including component C tends to shrink the contact lens immersed in the liquid preparation, i.e., the liquid preparation tends to decrease the size of the lens. On the other hand, the liquid preparation for a contact lens which includes component C without including component B tends to swell the contact lens immersed in the liquid preparation, i.e., the liquid preparation tends to increase the size of the lens. For this reason, it is assumed that if components B and C are used together, the shrinkage and the swelling of the contact lens are off-set, so that changes in the lens size hardly occur.

The amount of the above-mentioned component C to be included in the liquid preparation is suitably determined according to the amount of component B to be included in the liquid preparation. In particular, component C is included in an amount sufficient to provide a molar ratio of component B and component C in a range of 1:20 to 1.3:1. If the amount of component C exceeds 20 mols per 1 mol of component B, the adsorption of component A on the contact lens cannot be effectively prevented. If the amount of component C is less than 1 mol per 1.3 mols of component B, the disinfecting effect is deteriorated, and deposits are easily generated. Within the above-mentioned range, a desirable molar ratio of component B and component C is about 1:15 to about 1.2:1, and preferably about 1:14 to about 1:1.

In the liquid preparation for contact lens according to the present invention, glycolic acid and/or asparatic acid are especially adopted among the acid compounds which generate the organic anion for component B, while component C, AMPD or a salt thereof is adopted among components which generate the organic cation. Due to this, the disinfecting effect of component A (disinfectant) is advantageously exhibited, whereby a sufficient disinfecting effect is assured even if the concentration of component A is very low. Moreover, changes in the size of the contact lens are prevented, so that the liquid preparation offers excellent compatibility with the lens. In addition, component B and component C are specifically used in combination in a predetermined ratio, so that the generation of deposits on the contact lens is effectively prevented when the contact lens is treated with the liquid preparation. In short, even if the contact lens is immersed in the liquid preparation which includes the above-mentioned components A, B and C for a long period of time, or if the contact lens is repeatedly immersed in the liquid preparation, crystals or powdery substances of the components of the liquid preparation are hardly deposited on the surfaces of the contact lens. Due to this, the field of view of the contact lens is preferably maintained.

The above-mentioned components B and C increase the osmotic pressure of the liquid preparation by being added to the liquid preparation, so that these components also have an effect as an isotonic agent. For this reason, components B and C are respectively added to and included in the liquid preparation within a quantitative range which does not exceed the intended osmotic pressure.

It is also desirable that the liquid preparation for a contact lens according to the present invention does not include sodium chloride, which is conventionally used as the isotonic agent to adjust the osmotic pressure. If the liquid preparation includes sodium chloride, the concentration of the sodium chloride in the liquid preparation needs to be restricted not to exceed 0.2 w/w %, and is preferably not higher than 0.1 w/w %. In other words, it is desirable that the content of sodium chloride included in the liquid preparation is 0 to 0.2 w/w %, and preferably 0 to 0.1 w/w %. If the content of sodium chloride exceeds 0.2 w/w %, the disinfecting effect of component A is extremely reduced, so that the intended disinfecting effect cannot be obtained.

The osmotic pressure of the liquid preparation for contact lens is generally within a range of about 250 to about 400 mOsm/kg, which is substantially equal to physiological osmotic pressure. In the present invention, the concentrations of the components of the liquid preparation are suitably determined so as to adjust the osmotic pressure to be within the above-mentioned range.

In addition to the above-mentioned components B and C, which function as isotonic agents, other isotonic agents, in particular, a neutral amino acid (component D) and/or an nonionic isotonic agent (component E) can also be added and included in the liquid preparation for contact lens according to the present invention. By further adding these isotonic agents, deposition of crystals and powdery substances on the contact lens is further effectively restricted, and the disinfecting effect of component A is more effectively exhibited. It is needless to mention that these isotonic agents are also used within a quantitative range so as not to exceed the intended value of the osmotic pressure of the liquid preparation.

Examples of the above-mentioned neutral amino acid include glycine, alanine, taurine, $\epsilon$-aminocaproic acid, etc., and any one of, or any combination of these neutral amino acids can be used. Among these, glycine is especially preferably adopted. This is because, if glycine is used in the liquid preparation, the generation of deposits on the contact lens is further effectively restricted, the disinfecting effect is enhanced, and the compatibility of the liquid preparation with the contact lens is improved.

If a neutral amino acid is added to the liquid preparation, it is desirable that the amount of the neutral amino acid is 0.1 to 4 w/w % of the liquid preparation. This is because if the amount of the neutral amino acid is less than 0.1 w/w %, it is difficult to obtain any effect due to the addition of the neutral amino acid (isotonic effect). On the other hand, if more than 4 w/w % of the neutral amino acid is added, the deposition of crystals and powdery substances on the contact lens can occur.

Examples of the above-mentioned nonionic isotonic agent include propylene glycol, glycerin, sugars, etc., and any one of, or any combination of these nonionic isotonic agents can be used. Among them, it is especially preferable to use propylene glycol. This is because propylene glycol can further effectively restrict the generation of depositions on the contact lens, and can advantageously lower the occurrences of eye irritation by increasing the viscosity of the liquid preparation.

Where the nonionic isotonic agent is added to the liquid preparation, it is desirable that the amount of the nonionic isotonic agent to be included in the liquid preparation is 0.1 to 1 w/w %. If the amount of the nonionic isotonic agent is less than 0.1 w/w %, it is difficult to obtain the isotonic effect and the effect of reducing the eye irritation due to the nonionic isotonic agent. On the other hand, if the amount of the nonionic isotonic agent included in the liquid preparation is more than 1 w/w %, the compatibility of the liquid preparation with the contact lens is adversely affected.

In addition, the liquid preparation for contact lens according to the present invention may further include, as needed, various known additives that are used in conventional liquid preparations for a contact lens, such as a surfactant, a chelating agent, a pH adjusting agent, a buffer, and a thickener. Any one, or any combination of these additives may be suitably selected and included in the liquid preparation of the present invention. Any conventionally known additives can be used, as long as they assure a high degree of safety to the living body without having an adverse influence on the configuration and the physical properties of the contact lens. These additives are added to the liquid preparation within a suitable concentration range so as not to adversely influence the functions and effects of the present invention.

The present ophthalmic composition may further include a known surfactant as a cleaning agent, in order to advantageously exhibit a removal effect (cleaning effect) with respect to deposits such as eye lipids.

Examples of the surfactant include polyglycerin fatty acid ester, polyoxyethylene alkylether, polyoxyethylne-polyoxypropylene block copolymer, polyoxyethylene-polyoxypropylene ethylene diamine, polyoxyethylene sorbitan fatty acid ester, condensation products of polyoxyethylene alkylphenyl ether and formaldehyde, polyoxyethylene hardened castor oil, polyoxyethylene alkylphenyl ether, polyoxyethylene glycerin fatty acid ester, polyoxyethylene sorbitol fatty acid ester, polyoxyethylene castor oil, polyoxyethylene sterol, polyoxyethylene hydrogenated sterol, polyoxyethylene fatty acid ester, polyoxyethylene-polyoxypropylere alkyl ether, polyoxyethylene lanoline alcohol, polyoxyethylene alkyl amine, polyoxyethylene alkyl amide, polyoxyethylene alkyl etherphosphoric acid, and polysorbate, and any one, or any combination of these surfactants.

The surfactant is advantageously used in a concentration range of about 0.001 to about 5 w/w %, preferably about 0.005 to about 2 w/w %, and more preferably about 0.01 to about 1 w/w %. If the amount of the surfactant added to the liquid preparation is too small, the cleaning effect will not be sufficient. On the other hand, if the amount of the surfactant added to the liquid preparation is too large, further improvements of the cleaning effects cannot be expected, and instead, this would cause eye irritation.

In order to prevent a metal ion such as calcium from being adsorbed on the contact lens, especially on a soft contact lens, it is desirable to add a chelating agent to the liquid preparation. Examples of suitable chelating agents include ethylenediamine tetraacetic acid (EDTA) and salts thereof, such as disodium salts of ethylenediamine tetraacetic acid (EDTA.2Na) and trisodium salts of ethylenediamine tetraacetic acid (EDTA.3Na). A chelating agent generally provided in a concentration range of about 0.01 to about 0.5 w/w % of the liquid preparation for contact lens.

Further, if the pH value of the liquid preparation for contact lens according to the present invention is too high or too low, it may cause irritation or other problems to the eyes. Therefore, it is generally preferable that the pH value of the liquid preparation for contact lens is adjusted to be within a range of 4.0 to 9.0, preferably 6.0 to 8.0, and especially around 7.0. For this reason, a suitable pH adjusting agent or buffer may be added, as required.

Examples of the pH adjusting agent which is used for adjusting the pH include sodium hydroxide and hydrochloric acid. However, these pH adjusting agents may also generate sodium ions and chloride ions, similar to sodium chloride as mentioned above. Therefore, it is needed to restrict the amount of the pH adjusting agent to be used in the liquid preparation to be extremely low. Where the liquid preparation includes ions which constitute strong electrolyte inorganic salts such as sodium chloride due to the addition of a strong alkali or a strong acid to the liquid preparation, it is desirable that the concentration of sodium chloride in the liquid preparation, including sodium chloride formed by the addition of the strong alkali or acid, is not higher than 0.2 w/w %, and more preferably not higher than 0.1 w/w %, as mentioned above.

Buffers to effectively keep the pH value of the liquid preparation for contact lens within the above-mentioned range, assuring safety to the eyes, are suitably selected among conventionally known various buffers. For assuring a high degree of safety to the eyes and reducing the influence on the contact lens, the buffer is preferably selected, for example, from among a citrate buffer, a phosphate buffer, a borate buffer, a carbonate buffer, tris(hydroxymethyl)aminomethane (TRIS) buffer, and a Good-Buffer, such as bis (2-hydroxyethyl)iminotris(hydroxymethyl)methane (Bis-Tris). The buffer is added to the liquid solution in an amount of about 0.01 to about 2 w/w %. Where a buffer which indicates a relatively strong ionic strength, such as phosphate or citrate, is used, the disinfecting effect may be obstructed by the buffer, so that the amount of such buffer needs to be made zero or minimized.

The present ophthalmic composition may further contain a thickener, as required. Examples of suitable thickeners include various gums such as heteropolysaccharides; synthetic organic high molecular compounds such as polyvinyl alcohol, poly-N-vinylpyrrolidone, polyethylene glycol, polypropylene glycol, polyacrylamide; cellulose derivatives such as hydroxy ethyl cellulose and hydroxypropyl methylcellulose, and starch derivatives.

In preparing the ophthalmic composition of the present invention which contains the above-mentioned components A, B and C, the ophthalmic composition can be easily obtained by simply dissolving the respective components in an aqueous medium, such as purified water or distilled water, similar to the preparation of conventional solutions, without requiring any special methods.

The liquid preparation for a contact lens according to the present invention, which is obtained as described above, assures sufficient safety to the eyes, so that the ophthalmic composition can be preferably used as a contact lens disinfecting solution (disinfectant), a contact lens disinfecting and cleaning solution, a contact lens disinfecting and storing solution, a contact lens disinfecting, cleaning, and storing solution, etc. Moreover, since the liquid preparation for contact lens according to the present invention assures the safety to the eyes, the liquid preparation can be used as eye drops.

If a contact lens is treated with the liquid preparation according to the present invention, the contact lens, which has been removed from the eye, is placed in a suitable container filled with the liquid preparation of the present invention for a predetermined period of time, whereby the contact lens is disinfected. When it is needed to wear the contact lens again, the contact lens is taken out of the liquid preparation, and worn. In wearing the contact lens which has been disinfected as described above, there is only a need to rinse the contact lens with a physiological salt solution. Alternatively, the contact lens can be directly placed on the eye after the contact lens is taken out of the present liquid preparation, since the present liquid preparation is safe to the eyes.

The types of the contact lens that can be treated with the liquid preparation according to the present invention are not particularly limited. Examples of the contact lenses include soft contact lenses, which are classified into non-water-based contact lenses, low-water-content contact lenses, and high-water-content contact lenses, and hard contact lenses. Considering the properties of the liquid preparation according to the present invention, wherein the disinfectant (component A) is hard to be attached, the disinfectant has excellent compatibility with the lens and the deposition of crystals and powdery substances on the contact lens is restricted, so that the liquid preparation can be especially advantageously adopted for soft contact lenses, to which the disinfectant and the deposits are otherwise easily attached, and the sizes of which are otherwise easily changed.

EXAMPLES

To further clarify the concept of the present invention, some examples of the invention will be described. It is to be understood that the invention is not limited to the details of the illustrated examples and the foregoing description, but may be embodied with various changes, modifications and improvements, which may occur to those skilled in the art without departing from the scope of the invention defined in the attached claims.

Initially, to a sterilized purified water, predetermined additive components were respectively added according to the ratios shown in Table 1, and a suitable amount of a pH adjusting agent (hydrochloric acid or sodium hydroxide) was further added, as needed. Accordingly, liquid preparations of the Examples 1 to 19 were obtained, of which the osmotic pressure was about 290 mOsm/kg and the pH was about 7.3.

In preparing the liquid preparation for a contact lens, one of the following was used as component A: PHMB, which is a germicidal biguanide, and Polyquaternium-4, Polyquaternium-6, and Polyquaternium-22, which are germicidal quaternary ammonium salts. Glycolic acid or asparatic acid were used for component B, while AMPD was used for component C. In addition, glycine was used as a neutral amino acid (component D), while propylene glycol was used as a nonionic isotonic agent (component E). Moreover, HCO-60 (polyoxyethylene (60) hardened castor oil available from Japan Surfactant Kabushiki Kaisha) was used as a nonionic surfactant, while EDTA.2Na was used as a chelating agent. Furthermore, for the reason of comparison, compounds which have structures and characteristics similar to those of components B and C, and sodium chloride were respectively used. Lactic acid, gluconic acid, and citric acid were used as compounds similar to component B. 2-amino-2-methyl-1-propanol (AMP) and arginine were used as compounds similar to component C.

The following evaluation tests with respect to deposition of crystals and powdery substances were implemented for each of the thus obtained liquid preparations, and the results are shown in Table 1.

Evaluation of the Deposition

Soft contact lenses "Menicon SOFT MA" available from Menicon Co., Ltd., were immersed in each of the above-mentioned liquid preparations for four hours, and this operation was repeated 30 times. Subsequently, the surfaces of each of the contact lenses were visually observed, and evaluated in accordance with the following evaluation standards. Each of the liquid preparations was replaced with a respective new one after each operation of immersing the contact lens:

⊚: Very little change was observed, compared with the surfaces of the lens before the test;

○ Deposition of crystals and powdery substances was partially observed, to the extent of giving no problem in using the lens; and x: Deposition was observed on large part of the lens, or large deposits were observed.

TABLE 1

| | | | Example | | | | | | | | | |
|---|---|---|---|---|---|---|---|---|---|---|---|---|
| | | | 1 | 2 | 3 | 4 | 5 | 6 | 7 | 8 | 9 | 10 |
| Contents [w/w %] | A | PHMB | 1 ppm | 1 ppm | 1 ppm | 1 ppm | 1 ppm | 1 ppm | — | — | — | 1 ppm |
| | | Polyquaternium-4 | — | — | — | — | — | — | 100 ppm | — | — | — |
| | | Polyquaternium-6 | — | — | — | — | — | — | — | 100 ppm | — | — |
| | | Polyquaternium-22 | — | — | — | — | — | — | — | — | 100 ppm | — |
| | B | Glycolic acid | 0.10 | 0.40 | 1.00 | — | 0.50 | 0.50 | 0.50 | 0.50 | 0.50 | 1.00 |
| | | Asparatic acid | — | — | — | 0.50 | — | — | — | — | — | — |
| | (B') | Lactic acid | — | — | — | — | — | — | — | — | — | — |
| | | Gluconic acid | — | — | — | — | — | — | — | — | — | — |
| | | Citric acid | — | — | — | — | — | — | — | — | — | — |

TABLE 1-continued

|  |  |  |  |  |  |  |  |  |  |  |  |
|---|---|---|---|---|---|---|---|---|---|---|---|
|  | C | AMPD | 1.65 | 1.60 | 1.45 | 1.60 | 0.73 | 0.73 | 0.73 | 0.73 | 0.73 | 1.00 |
|  | (C') | AMP | — | — | — | — | — | — | — | — | — | — |
|  |  | Arginine | — | — | — | — | — | — | — | — | — | — |
|  | D | Glycine | — | — | — | — | 0.50 | 0.50 | 0.50 | 0.50 | 0.50 | — |
|  | E | Propylene glycol | — | — | — | — | 0.50 | 0.40 | 0.50 | 0.50 | 0.50 | — |
|  |  | HCO-60 | — | — | — | — | — | 0.05 | 0.05 | 0.05 | 0.05 | — |
|  |  | EDTA · 2Na | — | — | — | — | — | 0.05 | 0.05 | 0.05 | 0.05 | — |
|  |  | NaCl | — | — | — | — | — | — | — | — | — | — |
| B:C (molar ratio) |  |  | 1:12 | 1:3 | 1:1 | 1:4 | 1:1 | 1:1 | 1:1 | 1:1 | 1:1 | 1.4:1 |
| Amount of NaCl in the solution (w/w %) |  |  | 0 | 0 | 0 | 0 | 0 | <0.1 | <0.1 | <0.1 | <0.1 | 0 |
| Deposition of crystals |  |  | ○ | ○ | ○ | ○ | ◎ | ◎ | ◎ | ◎ | ◎ | X |

|  |  |  | Example |  |  |  |  |  |  |  |  |
|---|---|---|---|---|---|---|---|---|---|---|---|
|  |  |  | 11 | 12 | 13 | 14 | 15 | 16 | 17 | 18 | 19 |
| Contents [w/w %] | A | PHMB | 1 ppm | 1 ppm | 1 ppm | 1 ppm | 1 ppm | 1 ppm | 1 ppm | 1 ppm | 1 ppm |
|  |  | Polyquaternium-4 | — | — | — | — | — | — | — | — | — |
|  |  | Polyquaternium-6 | — | — | — | — | — | — | — | — | — |
|  |  | Polyquaternium-22 | — | — | — | — | — | — | — | — | — |
|  | B | Glycolic acid | 1.00 | 1.00 | 0.50 | 0.50 | — | — | — | — | — |
|  |  | Asparatic acid | — | — | — | — | 0.50 | — | — | — | — |
|  | (B') | Lactic acid | — | — | — | — | — | 0.50 | — | — | — |
|  |  | Gluconic acid | — | — | — | — | — | — | 0.50 | — | — |
|  |  | Citric acid | — | — | — | — | — | — | — | 0.50 | — |
|  | C | AMPD | 0.70 | 0.20 | — | — | — | 1.60 | 1.60 | 2.00 | — |
|  | (C') | AMP | — | — | 1.40 | — | — | — | — | — | — |
|  |  | Arginine | — | — | — | 2.85 | 2.85 | — | — | — | — |
|  | D | Glycine | — | — | — | — | — | — | — | — | 0.50 |
|  | E | Propylene glycol | — | — | — | — | — | — | — | — | 0.50 |
|  |  | HCO-60 | — | — | — | — | — | — | — | — | 0.05 |
|  |  | EDTA · 2Na | — | — | — | — | — | — | — | — | 0.05 |
|  |  | NaCl | — | — | — | — | — | — | — | — | 0.43 |
| B:C (molar ratio) |  |  | 2:1 | 7:1 |  |  |  |  |  |  |  |
| Amount of NaCl in the solution (w/w %) |  |  | 0 | 0 | 0 | 0 | 0 | 0 | 0 | 0 | 0.43 |
| Deposition of crystals |  |  | X | X | X | X | X | X | X | X | ○ |

(B') and (C') in the above TABLE 1 are similar to the component B and C, respectively, in terms of the structure or the component.

As is apparent from the results shown in Table 1, the evaluations of the deposition of the liquid preparations of Examples 1 to 9, in which components A, B and C are included and components B and C are combined to fulfill the predetermined molar ratio, were ◎ or ○. From these results, it is understood that the generation of deposits on the contact lenses is advantageously restricted. In particular, in Examples 5 to 9, to which component D and component E are further added, in addition to components A, B and C, the evaluations of deposition were ◎, so that an especially excellent effects are exhibited.

On the other hand, although components of A, B and C are used in combination in the liquid preparations of Examples 10 to 12, deposits were generated on the lenses, because the molar ratio of component B and component C were within 1.4:1 to 7:1. In addition, deposits were also generated in the liquid preparations of Examples 13 to 18, in which compounds similar to component B or component C were used. The evaluation of deposition of Example 19, whose osmotic pressure was adjusted by sodium chloride, was ○.

The following evaluation tests with respect to the disinfecting effects were implemented for Examples 1 to 9 and 19, which were evaluated as ◎ or ○ in the above-mentioned evaluations of the deposition. Thus obtained results were shown in the following Table 2.

Test for Examining the Disinfecting Effect 9.9 mL of each of the solutions was put into respective test tubes. To each of the test tubes, there was added 0.1 mL of a fungi liquid, which contained C.a. (*Candida albicans* IFO 1594) as the test bacteria or fungi in an amount of $10^7$ to $10^8$ cfu/mL, so as to provide a fungal suspension including the fungi in an amount of $10^5$ to $10^6$ cfu/mL. The thus obtained specimens were kept at 23° C. for four hours. Thereafter, 1 mL of each fungi suspension was taken out of each of the test tubes as a sample, and viable cell count per 1 mL of each suspension was measured by using 20 mL of Glucose Peptone agar medium, by plate dilution method. On the basis of the obtained value, the viable cell count per 1 ml, of each fungi suspension was calculated. Then, for each of the ophthalmic compositions, the amount of the reduction of the fungi was calculated in logarithm (log reduction) according to the following equation:

Log reduction=log (viable cell count per 1 mL of each specimen immediately after inoculation)−log (viable cell count per 1 mL of each fungi suspension after treatment by each liquid preparation for contact lens specimens).

The disinfecting effects were evaluated based on thus obtained values of the log reduction, in accordance with the following evaluation standards:

◎: The log reduction was not less than 2 (there was a considerable disinfecting effect);

○: The log reduction was not less than 1 and less than 2 (there was a disinfecting effect); and x: The log reduction was less than 1 (the disinfecting effect was weak).

TABLE 2

| | Example | | | | | | | | | |
|---|---|---|---|---|---|---|---|---|---|---|
| | 1 | 2 | 3 | 4 | 5 | 6 | 7 | 8 | 9 | 19 |
| Disinfecting effect | ○ | ○ | ⊚ | ○ | ⊚ | ⊚ | ○ | ⊚ | ○ | X |
| Log reduction | 1.68 | 1.84 | 2.12 | 1.61 | 2.52 | 2.38 | 1.00 | 2.36 | 1.44 | 0.55 |

As is apparent from the results in Table 2, the disinfecting effects of the liquid preparations of Examples 1 to 9 were evaluated as ⊚ or ○, which shows that the disinfecting effects were advantageously exhibited. In particular, excellent disinfecting effects can be realized by the liquid preparations of Examples 3, 5, and 6, in which PHMB has been used as the disinfectant and B:C (molar ratio)=1:1, although the concentration of the disinfectant in the liquid preparation was 1 ppm.

On the other hand, very little disinfecting effects were exhibited by the disinfectant of the Example 19, whose osmotic pressure was adjusted by sodium chloride, although the same amount of the disinfectant was added to the liquid preparation.

What is claimed is:

1. A liquid preparation for a contact lens comprising:
   a component (A) comprising at least one disinfectant selected from the group consisting of germicidal biguanides and germicidal quaternary ammonium salts;
   a Component (B) comprising at least one of glycolic acid and asparatic acid; and
   a Component (C) comprising one of 2-amino-2-methyl-1,3-propanediol and a salt thereof;
   wherein a molar ratio of said Component B and said Component C is in a range of 1:20 to 1.3:1.

2. The liquid preparation for a contact lens according to claim 1, wherein the preparation optionally further comprises sodium chloride, and the concentration of sodium chloride in said liquid preparation is adjusted to be in a range of 0 to 0.2 w/w %.

3. The liquid preparation for a contact lens according to claim 1, wherein said Component A is included in a concentration of 0.1 to 500 ppm.

4. The liquid preparation for a contact lens according to claim 1, wherein said Component B is included in a concentration of 0.01 to 5 w/w %.

5. The liquid preparation for a contact lens according to claim 1, further comprising a neutral amino acid.

6. The liquid preparation for a contact lens according to claim 5, wherein said neutral amino acid is included in a concentration of 0.1 to 4 w/w %.

7. The liquid preparation for a contact lens according to claim 5, wherein said neutral amino acid is glycine.

8. The liquid preparation for a contact lens according to claim 1, further comprising propylene glycol.

9. The liquid preparation for a contact lens according to claim 8, wherein a concentration of said propylene glycol is in a range of 0.1 to 1 w/w %.

10. The liquid preparation for a contact lens according to claim 1, further comprising at least one of a surfactant and a chelating agent.

11. The liquid preparation for a contact lens according to claim 1, wherein said contact lens to be treated with said liquid preparation is a soft contact lens.

* * * * *